United States Patent
Alavi et al.

(10) Patent No.: US 8,900,862 B2
(45) Date of Patent: *Dec. 2, 2014

(54) MESH ENCLOSED TISSUE CONSTRUCTS

(75) Inventors: Sayedhamed Alavi, Irvine, CA (US); Arash Kheradvar, Irvine, CA (US)

(73) Assignee: The Regents of the University of California, Oakland, AS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/427,843

(22) Filed: Mar. 22, 2012

(65) Prior Publication Data
US 2012/0244617 A1 Sep. 27, 2012

Related U.S. Application Data

(60) Provisional application No. 61/466,882, filed on Mar. 23, 2011, provisional application No. 61/496,369, filed on Jun. 13, 2011, provisional application No. 61/540,330, filed on Sep. 28, 2011, provisional application No. 61/559,694, filed on Jan. 19, 2012.

(51) Int. Cl.

| | |
|---|---|
| C12N 5/071 | (2010.01) |
| A61F 2/06 | (2013.01) |
| A61F 2/24 | (2006.01) |
| A61L 27/34 | (2006.01) |
| C12N 5/00 | (2006.01) |
| A61L 27/54 | (2006.01) |
| A61L 27/38 | (2006.01) |
| A61L 27/56 | (2006.01) |
| A61L 27/04 | (2006.01) |

(52) U.S. Cl.
CPC .............. *C12N 5/0068* (2013.01); *A61L 27/34* (2013.01); *C12N 2501/15* (2013.01); *A61L 27/54* (2013.01); *A61F 2/2415* (2013.01); *A61L 2400/18* (2013.01); *C12N 5/0691* (2013.01); *A61L 27/3826* (2013.01); *A61L 27/56* (2013.01); *A61L 2300/414* (2013.01); *A61L 27/3804* (2013.01); *C12N 2533/54* (2013.01); *A61L 27/047* (2013.01); *C12N 2533/10* (2013.01); *A61L 27/3808* (2013.01); *A61L 2430/20* (2013.01); *A61L 27/3886* (2013.01)
USPC ......................... 435/373; 435/402; 623/23.72

(58) Field of Classification Search
USPC ................................ 435/373, 402; 623/23.72
See application file for complete search history.

(56) References Cited

U.S. PATENT DOCUMENTS

| | | |
|---|---|---|
| 4,191,218 A | 3/1980 | Clark et al. |
| 6,103,255 A | 8/2000 | Levene et al. |

(Continued)

OTHER PUBLICATIONS

Liu et al., Surface modification of titanium, titanium alloys, and realted materials for biomedical applications. Materials Science and Engineering R. vol. 47 (2004) pp. 49-121.*

(Continued)

*Primary Examiner* — Jon P Weber
*Assistant Examiner* — Kara Johnson
(74) *Attorney, Agent, or Firm* — Knobbe Martens Olson & Bear, LLP

(57) ABSTRACT

Described is a scaffold that is strong enough to resist forces that exist inside a body, while possessing biocompatible surfaces. The scaffold is formed of a layer of mesh (e.g., Stainless Steel or Nitinol) that is tightly enclosed by a multi-layer biological matrix. The biological matrix can include three layers, such a first layer (smooth muscle cells) formed directly on the metal mesh, a second layer (fibroblast/myofibroblast cells) formed on the first layer, and a third layer (endothelial cells) formed on the second layer. The scaffold can be formed to operate as a variety of tissues, such as a heart valve or a vascular graft. For example, the mesh and corresponding biological matrix can be formed as leaflets, such that the scaffold is operable as a tissue heart valve.

23 Claims, 13 Drawing Sheets

(56) References Cited

U.S. PATENT DOCUMENTS

| | | | |
|---|---|---|---|
| 6,139,575 A | 10/2000 | Shu et al. |
| 6,337,198 B1 | 1/2002 | Levene et al. |
| 6,461,382 B1 | 10/2002 | Cao |
| 7,422,603 B2 | 9/2008 | Lane |
| 7,575,759 B2 | 8/2009 | Murphy et al. |
| 7,635,592 B2 | 12/2009 | West et al. |
| 7,846,728 B2 | 12/2010 | Brooks et al. |
| 7,871,435 B2 | 1/2011 | Carpentier et al. |
| 7,914,808 B2 | 3/2011 | Malaviya et al. |
| 7,968,026 B1 | 6/2011 | Teoh et al. |
| 7,972,377 B2 | 7/2011 | Lane |
| 8,017,396 B2 | 9/2011 | Kumar |
| 8,039,258 B2 | 10/2011 | Harris et al. |
| 8,071,007 B1 | 12/2011 | Teoh et al. |
| 8,137,686 B2 | 3/2012 | Kladakis et al. |
| 2003/0027332 A1 | 2/2003 | Lafrance et al. |
| 2005/0002982 A1 | 1/2005 | Mooney et al. |
| 2005/0143810 A1 | 6/2005 | Dauner et al. |
| 2005/0181016 A1 | 8/2005 | Freyman et al. |
| 2006/0246584 A1 | 11/2006 | Covelli |
| 2006/0253192 A1* | 11/2006 | Atala et al. ............... 623/2.13 |
| 2007/0041952 A1 | 2/2007 | Guilak et al. |
| 2009/0163612 A1 | 6/2009 | Brady et al. |
| 2009/0252795 A1 | 10/2009 | Smyth |
| 2010/0249922 A1 | 9/2010 | Li et al. |
| 2012/0015331 A1 | 1/2012 | Wood et al. |

OTHER PUBLICATIONS

Misfeld et. al., Heart valve macro- and microstructure. Philos Trans R Soc Lond B Biol Sci. vol. 362 (2007) pp. 1421-1436.*
Jansen et al., Surgical mesh as a scaffold for tissue regeneration in the esophagus. European Surgical Research, vol. 36 (2004) pp. 104-111.*
Liu et al., Surface modification of titanium, titanium alloys, and related materials for biomedical applications. Materials Science and Engineering R. vol. 47 (2004) pp. 49-121.*
Misfeld et al., Heart valve macro-and microstructure. Phil. Trans. R. Soc. B. vol. 362 (2007), pp. 1421-1436.*
Trepanier, C. et al. 2000 "Corrosion Resistance and Biocompatibility of Passivated Nitinol" in *Shape Memory Implants* (ed.) L'H. Yahia, ndc, pp. 35-45.
Van Der Merwe, H. et al 2008 "A computational study of knitted Nitinol meshes for their prospective use as external veil reinforcement" *Journal of Biomechanics* 41: 1302-1309.
Abu-Omar, Y. et al. 2008 "Prosthetic heart valves" Surgery 26: 496-500.
Alavi, S.H. et al. 2011 "A hybrid self-regenerative tissue approach as a proper alternative for prosthetic heart valves" *ASAIO J* 57: p. 88.
Alavi, H. et al. 2011 "A hybrid self-renewal engineered tissue for heart valve leaflets" Society of Heart Valve Disease, 6th Biennial Meeting (Abstract).
Apte, S.S. et al. 2011 "Current developments in the tissue engineering of autologous heart valves: moving towards clinical use" Future Cardiology 7: 77-97.
Fong, P. et al. 2006 "The use of polymer based scaffolds in tissue-engineered heart valves" Progress in Pediatric Cardiology 21: 193-199.
Mulholland D.L. and Gotlieb, A.I. 1996 "Cell biology of valvular interstitial cells" Can J Cardiol 12: 231-236.
Syedain, Z.H. et al. 2009 "Controlled Cyclic Stretch Bioreactor for Tissue-Engineered Heart Valves" Biomaterials 30: 4078-4084.
Van Den Broek, C.N. et al. 2008 "Medium with blood-analog mechanical properties for cardiovascular tissue culturing" Bioreheology 45: 651-661.
Zund, G. et al. 1998 "Tissue engineering: A new approach in cardiovascular surgery; Seeding of human fibroblasts followed by human endothelial cells on resorbable mesh" *European Journal of Cardio-thoracic Surgery* 13: 160-164.
d'Arcy JL. Prendergast BD, Chambers JB, Ray SG, Bridgewater B. Valvular heart disease: The next cardiac epidemic. Heart. 2011;97:91-93.
Nikomo VT, Gardin JM, Skelton TN, Gottdiener JS, Scott CG, Enriquez-Sarano M. Burden of valvular heart diseases: A population-based study. Lancet. 2006;368:1005-1011.
Abu-Omar Y. Ratnatunga CP. Prosthetic heart valves. Surgery (Oxford). 2008;26:496-500.
Kheradvar A, Gorman RC, Gorman JH, III, Zeeschan A, Gharib M. Evaluation of isovolumic relaxation phase in the process of ventricular remoldeling following myocardial infarction. Engineering in Medicine and Biology Society. 2004. IEMBS '04. 26th Annual International Conference of the IEEE. 2004;2:3654-3657.
Shah SR VN. The effect of glycosaminoglycan stabilization on tissue buckling in bioprosthetic heart valves. Biomaterials. 2008;29:1645-1653.
Apte SS, Paul A, Prakash S, Shum-Tim D. Current developments in the tissue engineering of autologous heart valves: Moving towards clinical use. Future Cardiology. 2011;7:77-97.
Stephens EH, de Jonge N, McNeill MP, Durst CA, Grande-Allen KJ. Age-related changes in material behavior of porcine mitral and aortic valves and correlation to matrix composition. Tissue Engineering Part A. 2010;16:867-878.
Hoffmann G, Lutter, G., Cremer, J. Durability of bioprosthetic cardiac valves. Dtsch Arztebl Int. 2008;105:143-148.
Syedain ZH, Tranquillo RT. Controlled cyclic stretch bioreactor for tissue-engineered heart valves. Biomaterials. 2009;30:4078-4084.
Vesely I, Bougher D, Song T. Tissue bucking as a mechanism of bioprosthetic valve failure. Ann Thorac Surg. 1988;46:302-308.
Thubrikar M, Deck J, Aouad J, S. N., Role of mechanical stress in calcification of aortic bioprosthetic valves. J Thorac Cardiovasc Surg. 1983,86.115-125.
Smith DB, Sacks MS, Pattany PM, Schroeder R., Fatigue-induced changes in bioprosthetic heart valve three dimensional geometry and the relation to tissue damage. J Heart Valve Dis. 1999;8.
Adamczyk MM, Vesely I. Biaxial strain distributions in explanted porcine bioprosthetic valves. J Heart Valve Dis. 2002;11:688-695.
Vesely I, Barber JE, Ratliff NB. Tissue damage and calcification may be independent mechanisms of bioprosthetic heart valve failure. J Heart Valve Dis. 2001;10:471-477.
Ferrans VJ, Spray TL, Billingham ME, Roberts WC. Structural changes in glutaraldehyde-treated porcine heterografts used as substitute cardiac valves: Transmission and scanning electron microscopic observations in 12 patients. Am J Cardiol. 1978;41:1159-1184.
Mendelson K. Schoen F. Heart valve tissue engineering: Concepts, approaches, progress, and challenges. Annals of Biomedical Engineering. 2006;34:1799-1819.
Breuer CK, Mettler BA, Anthony T, Sales VL, Schoen FJ, Mayer JE, Application of tissue-engineering principles toward the development of a semilunar heart valve substitute. Tissue Engineering. 2004;10:1725-1736.
Rabkin E, Schoen FJ. Cardiovascular tissue engineering. Cardiovascular Pathology. 2002;11:305-317.
Rabkin-Aikawa E, Mayer, J.E. Jr., Schoen, F.J. Heart valve regeneration. Adv Biochem Eng Biotechnol. 2005;94:141-179.
Vesely I. Heart valve tissue engineering. Circ Res. 2005;97:743-755.
Sacks MS, Schoen FJ, Mayer JE. Bioengineering challenges for heart valve tissue engineering. Annual Review of Biomedical Engineering. 2009;11:289-313.
Shinoka T, Breuer, C.K., Tanel, R.E., Zund, G., Miura, T., Ma, P.X., Langer, R., Vacanti, J.P., Mayer, J.E. Jr. Tissue engineering heart valves. Valve leaflet replacement study in a lamb model. Ann Thorac Surg. 1995,60.S513-516.
Shinoka T, Ma, P.X., Shum-Tim, D., Breuer, C.K., Cusick, R.A., Zund, G., Langer, R., Vacanti, J.P., Mayer, J.E. Jr. Tissue-engineered heart valves. Autologous valve leaflet replacement study in a lamb model. Circulation. 1996;94:164-168.
Hoerstrup SP, Sodian R, Daebritz S. Wang J, Bacha EA, Martin DP, Moran AM, Guleserian KJ, Sperling JS, Kaushal S. Vacanti JP, Shoen FJ, Mayer JE, Jr. Functional living trileaflet heart valves grown in vitro. Circulation. 2000;102:III-44-49.
Steinhoff G, Stock U, Karim N, Mertsching H, Timka A, Meliss RR, Pethig K, Haverich A, Bader A. Tissue engineering of pulmonary heart valves on allogenic acellular matrix conduits : In vivo restora-

(56) References Cited

OTHER PUBLICATIONS tion of valve tissue. Circulation. 2000;102:III-50-55, References Cited p. 76. Principal Investigator/Program Director (Last, first, middle): Kheradvar, Arash.
van Geemen D, Riem Vis P, Soekhradj—Soechit S, Sluijter J, de Liefde—van Beest M, Kluin J, Bouten C. Decreased mechanical properties of heart valve tissue constructs cultured in platelet lysate as compared to fetal bovine serum. Tissue Engineering Part C Methods. 2011:online ahead of editing.
Grande-Allen K, Liao J. The heterogeneous biomechanics and mechanobiology of the mitral valve: Implications for tissue engineering. Current Cardiology Reports. 2011;13:113-120.
Flanagan TC, Pandit, A. Living artificial heart valve alternatives: A review. Eur Cell Mater. 2003;6:28-45.
Boontheekul T, Mooney DJ. Protein-based signaling systems in tissue engineering. Current Opinion in Biotechnology. 2003;14:559-565.
Alavi SH, Kheradvar, A. A hybrid self-regenerative tissue approach as a proper alternative for prosthetic heart valves. ASAIO J. 2011;57: p. 88.
Kheradvar A, Milano M, Goman RC, Gorman JH, III. Gharib M. Estimation of elastic and viscous properties of the left ventricle based on annulus plane harmonic behavior. Conference Proceedings. Annual International Conference of the IEEE Engineering in Medicine and Biology Society (IEEE Cat., No. 06CH37748). 2006:4 pp.-4 pp. 4 pp.
Pypen CMJM, Plenk Jr H, Ebel MF, Svagera R, Wemisch J. Characterization of microblasted and reactive ion etched surfaces on the commercially pure metals niobium, tantalum and titanium. Journal of Materials Science: Materials in Medicine. 1997;8:781-784.
Oshida Y, Sachdeva R, Miyazaki S, Daly J. Effects of shot-peening on surface contact angles of biomaterials. Journal of Materials Science. Materials in Medicine. 1993,4.443-447.
Alavi SH, Kheradvar, A. Metal mesh scaffold for tissue engineering of membranes. Tissue Eng Part C. 2011; Tissue Engineering: Part C, vol. 18, No. 4, 2012, Mary Ann Liebert, Inc., DOI: 10.1089/ten.tec.2011.0531.
Boyan BD, Hummert, T.W., Dean, D.D., and Schwartz, Z. Role of material surfaces in regulating bone and cartilage cell responses. Biomaterials. 1996;17:137.
Kieswener K, Schwartz, Z., Hummert, T. W., and Cochran, D. L. Surface roughness modulates the local production of growth factors and cytokines by osteoblast-like mg-63 cells. J Biomed Mater Res. 1996;32:55.
Alavi SH, Kheradvar, A. A hybrid self-renewal engineered tissue for heart valve leaflets. Society of Heart Valve Disease 6th Biennial Meeting. 2011.
Leitao E. Barbosa MA, De Groot K. In vitro testing of surface-modified biomaterials. Journal of Materials Science: Materials in Medicine. 1998;9:543-548.
Shenton MJ, Bradley JW, van den Berg JA, Armour DG, Stevens GC. Ultralow energy ion beam surface modification of low density polyethylene. The Journal of Physical Chemistry B. 2005;109:22085-22088.
Pignataro B, Conte E, Scandurra A, Marletta G. Improved cell adhesion to ion beam-irradiated polymer surfaces. Biomaterials. 1997;18:1461-1470.
Maitz MF, Pham MT, Matz W, Reuther H, Steiner G, Richter E. Ion Beam treatment of titanium surfaces for enhancing deposition of hydroxyapatite from solution. Biomolecular Engineering. 2002;19:269-272.
Kondyurin A, Pecheva E, Pramatarova L. Calcium phosphate formation on plasma immersion ion implanted low density polyethylene and polytetrafluorethylene surfaces. Journal of Materials Science: Materials in Medicine. 2008;19:1145-1153.
Gen BK, Kondyunn A, Bilek MMM. Comparison of protein surface attachment on untreated and plasma immersion ion implantation treated polystyrene: Protein islands and carpet. Langmuir. 2007;23:2741-2746.

Walachova K, Svorcik V, Bacáková L, Hnatowicz V. Colonization of ion-modified polyethylene with vascular smooth muscle cells in vitro. Biomaterials. 2002,33.2989-2996.
Sugita Y, Suzuki Y, Someya K, Ogawa A, Furuhata H, Miyoshi S, Motomura T, Miyamoto H, Igo S, Nosé Y. Experimental evaluation of a new antithrombogenic stent using ion beam surface modification. Artificial Organs. 2009;33:456-463.
Appleton AJE, Appleton CTG, Boughner DR, Rogers KA. Vascular smooth muscle cells as a valvular interstitial cell surrogate in heart valve tissue engineering. Tissue Engineering Part A. 2009;15:3889-3897.
Tedder MESA, Chen J, Liao J, Simionescu DT. Assembly and testing of stem cell-seeded layered collagen constructs for heart valve tissue engineering. Tissue Eng Part A. 2010;17:25-36.
Long J, and Tranquillo, RT. Elastic fiber production in cardiovascular tissue-equivalents Matrix Biology. 2003;22:339-350, References Cited p. 77, Principal Investigator/Program Director (Last, first, middle): Kheradvar, Arash.
Khaled A, and S. Durum. Lymphocide: Cytokines and the control of lymphoid homeostasis. Nat Rev Immunol. 2002;2:817-830.
Hori J, and T. Ng. Neural progenitor cells lack immunogenicity and resist destruction as allografts. Stem Cells. 2003;21:405-416.
Rabkin-Aikawa E, Farber, M., Aikawa, M., Schoen, F.J. Dynamic and reversible changes of interstitial cell phenotype during remodeling of cardiac valves. J Heart Valve Dis. 2004;13:841-847.
Mulholland DL. Gottieb, A.I. Cell biology of valvular interstitial cells. Can J Cardiol. 1996;12:231-236.
Aikawa E, Whittaker, P., Farber, M., Mendelson, K., Padera, R.F., Aikawa, M., and Schoen, F.J. Human semilunar cardiac valve remodeling by activated cells from fetus to adult: Implications for postnatal adaptation, pathology, and tissue engineering. Circulation. 2006;113:1344-1352.
Wirrig EE, Hinton RB, Yutzey KE, Differential expression of cartilage and bone-related proteins in pediatric and adult diseased aortic valves. Journal of Molecular and Cellular Cardiology. 2011;50:561-569.
Liu AC, Joeg VR, Gotieb AI. The emerging role of valve interstitial cell phenotypes in regulating heart valve pathobiology. Am J Pathol. 2007;171:1407-1418.
M.S. Hahn MKM, E. Wang, R. Schmedlen, J. West. Physiologic pulsatile flow bioreactor conditioning of poly(ethylene glycol)-based tissue engineered vascular grafts. Annals of Biomedical Engineering. 2007;35:190-200.
Tranquillo ZHSaRT. Controlled cyclic stretch bioreactor for tissue-engineered heart valves. Biomaterials. 2009;30:4078-4064.
Ku CH, P. H. Johnson, P. Batten, P. Sarathchandra, R. C. Chambers, P. M. Taylor, M. H. Yacoub, and A. H. Chester. . Collagen synthesis by mesenchymal stem cells and aortic valve interstitial cells in response to mechanical stretch. Cardiovasc. Res. 2006;71:548-556.
Butcher JT, S. Tressel, T. Johnson, D. Turner, G. Sorescu, H. Jo. and R. M. Nerem. . Profiles of valvular and vascular endothelial cells reveal phenotypic differences: Influence of shear stress. Arterioscler. Thromb. Vasc. Biol. 2006;26:69-77.
Kheradvar A, Falahatpisheh, A. The effects of dynamic saddle annulus and leaflet length on transmitral flow pattern and leaflet stress of a bi-leaflet bioprosthetic mitral valve. J Heart Valve Dis. 2011; The Edwards Lifesciences Center for Advanced Cardiovascular Technology. The Henry Samueli School of Engineering, University of California, Irvine. Irvine, CA, USA, J Heart Valve Dis, vol. 21. No. 2, Mar. 2012.
Kheradvar A, Gharib M. On mitral valve dynamics and its connection to early diastolic flow. Annals of Biomedical Engineering. 2009,37. 1-13.
Kheradvar A, Kasalko J, Johnson D, Gharib M. An in vitro study of changing profile heights in mitral bioprostheses and their influence on flow. Asaio Journal. 2006;52:34-38.
van den Broek CN, Pullens RAA, Frøbert O, Ruten MCM, den Hartog WF, van de Vosse FN. Medium with blood-analog mechanical properties for cardiovascular tissue culturing. Biorheology. 2008;45:651-661.
Hildebrant J, Fukaya H, Martin CJ. Stress-strain relations of tissue sheets undergoing uniform twodimensional stretch. J Appl Physiol. 1969;27:758-762.

(56) References Cited

OTHER PUBLICATIONS

Zioupos P, Barbenel JC, Fisher J. Mechanical and optical anisotropy of bovine pericardium. Med Biol Eng Comput. 1992;30:76-82.
Schenke-Layland K. Non-invasive multiphoton imaging of extracellular matrix structures. J Biophotonics. 2008;1:451-462.
Schenke-Layland K, Madershahian N, Riemann I, Starcher B, Halbhuber KJ, Konig K, Stock UA. Impact of cryopreservation on extracellular matrix structures of heart valve leaflets. Ann Thorac Surg., 2006;81:918-926.
Chen J, Lee A, Zhao J, Wang H, Lui H, McLean DI, Zeng H. Spectroscopic characterization and microscopic imaging of extracted and in situ cutaneous collagen and elastic tissue components under two-photon excitation. Skin Res Technol. 2009;15:418-426.
Cox G, Kable E, Jones A, Fraser I, Manconi F, Gorrell MD. 3-dimensional imaging of collagen using second harmonic generation. J Struct Biol. 2003;141:53-62.
Georgiou E, Theodossiou T, Hovhannisyan V, Politopoulos K, Rapti GS, Yova D. Second and third optical harmonic generation in type i collagen, by nanosecond laser irradiation, over a broad spectral region. Optics Communications. 2000;176:253-260, References Cited p. 78, Principal Investigator/Program Director (Last, first, middle): Kheradvar, Arash.
Liu WF, Ma M, Bratlie KM, Dang TT, Langer R, Anderson DG. Real-time in vivo detection of biomaterial-induced reactive oxygen species. Biomaterials. 2011;32:1796-1801.
Ma M, Liu WF, Hill PS, Bratlie KM, Siegwart DJ, Chin J, Park M, Guerreiro J, Anderson DG. Development of cationic polymer coatings to regulate foreign-body responses. Advanced Materials. 2011,23.H189-H194.
McGuigan AP, Sefton MV. The thrombogenicity of human umbilical vein endothelial cell seeded collagen modules. Biomaterials. 2008;29:2453-2463.
Salvador-Morales C, Zhang L, Langer R, Farokhzad OC. Immunocompatibility properties of lipid-polymer hybrid nanoparticles with heterogeneous surface functional groups. Biomaterials. 2009;30:2231-2240.
Bobak D, Frank M, Tenner A, Characterization of c1q receptor expression on human phagocytic cells: Effects of pdbu and fmlp. The Journal of Immunology. 1986;136:4604-4610.
Saidi IS, Jacques SL, Tittel FK. Mie and rayleigh modeling of visible-light scattering in neonatal skin. Appl. Opt. 1995;34:7410-7418.
Na GC, Butz LJ, Bailey DG, Carroll RJ. In vitro collagen fibril assembly in glycerol solution: Evidence for a helical cooperative mechanism involving microfibrils. Biochemistry. 1986;25:958-966.
Kuznetsova N, Chi SL, Leikin S. Sugars and polyols inhibit fibrillogenesis of type i collagen by disrupting hydrogen-bonded water bridges between the helices. Biochemistry. 1998;37:11888-11895.
Deymier-Black AC, Almer JD, Stock SR, Haeffner DR, Dunand DC. Synchrotron x-ray diffraction study of load partitioning during elastic deformation of bovine dentin. Acta Biomater. 2010;6:2172-2180.
Yeh AT, Choi B, Nelson JS, Tromberg BJ. Reversible dissociation of collagen in tissues. 2003;121:1332-1335.
Wells PB, Yeh AT, Humphrey JD. Influence of glycerol on the mechanical reversibility and thermal damage susceptibility of collagenous tissues. IEEE Trans Biomed Eng. 2006;53:747-753.
Liu YC, Chiang AS. High-resolution confocal imaging and three-dimensional rendering. Methods. 2003;30:86-93.
Hara M, Dizon RF, Glick BS, Lee CS, Kaestner KH, Piston DW, Bindokas VP. Imaging pancreatic betacells in the intact pancreas. Am J Physiol Endocrinol Metab. 2006;290.E1041-1047.
Iijima K. Liu HP, Chiang AS, Heam SA, Konsolaki M, Zhong Y. Dissecting the pathological effects of human abeta40 and abeta42 in drosophila: A potential model for alzheimer's disease. Proc Natl Acad Sci U S A. 2004;101:6623-6628.
Kheradvar A, Milano M, Gorman R, Gorman J. Gharib M. Assessment of left ventricular viscoelastic components based on ventricular harmonic behavior. Cardiovascular Engineering. 2006;6:30-39.

* cited by examiner

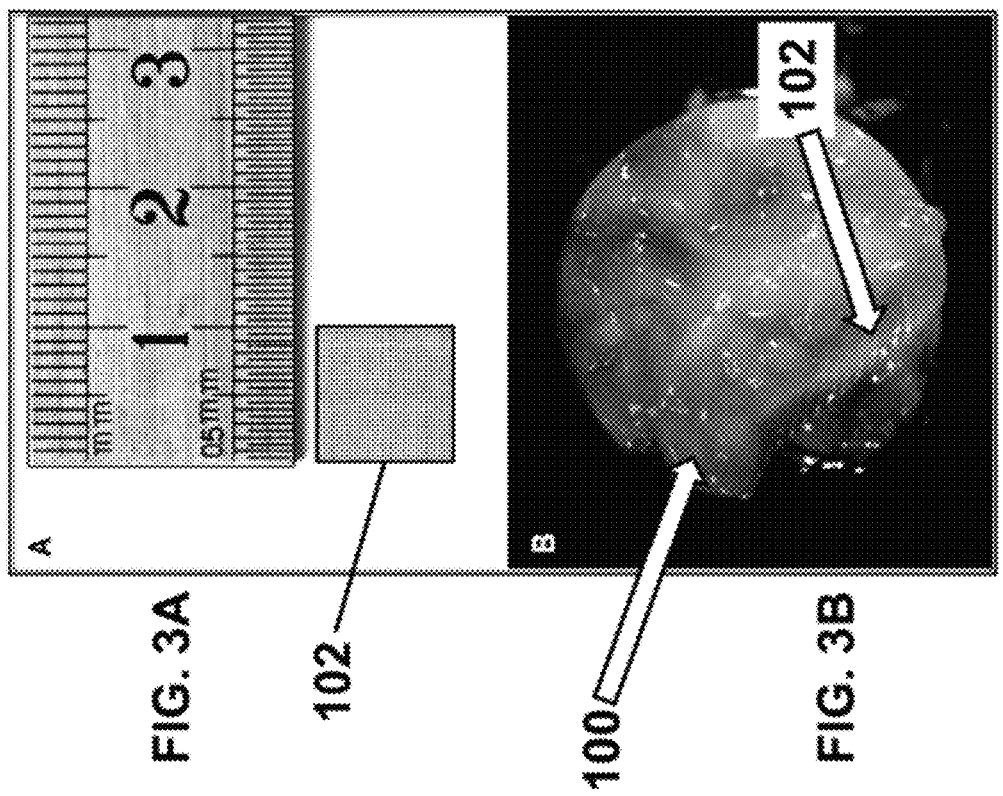

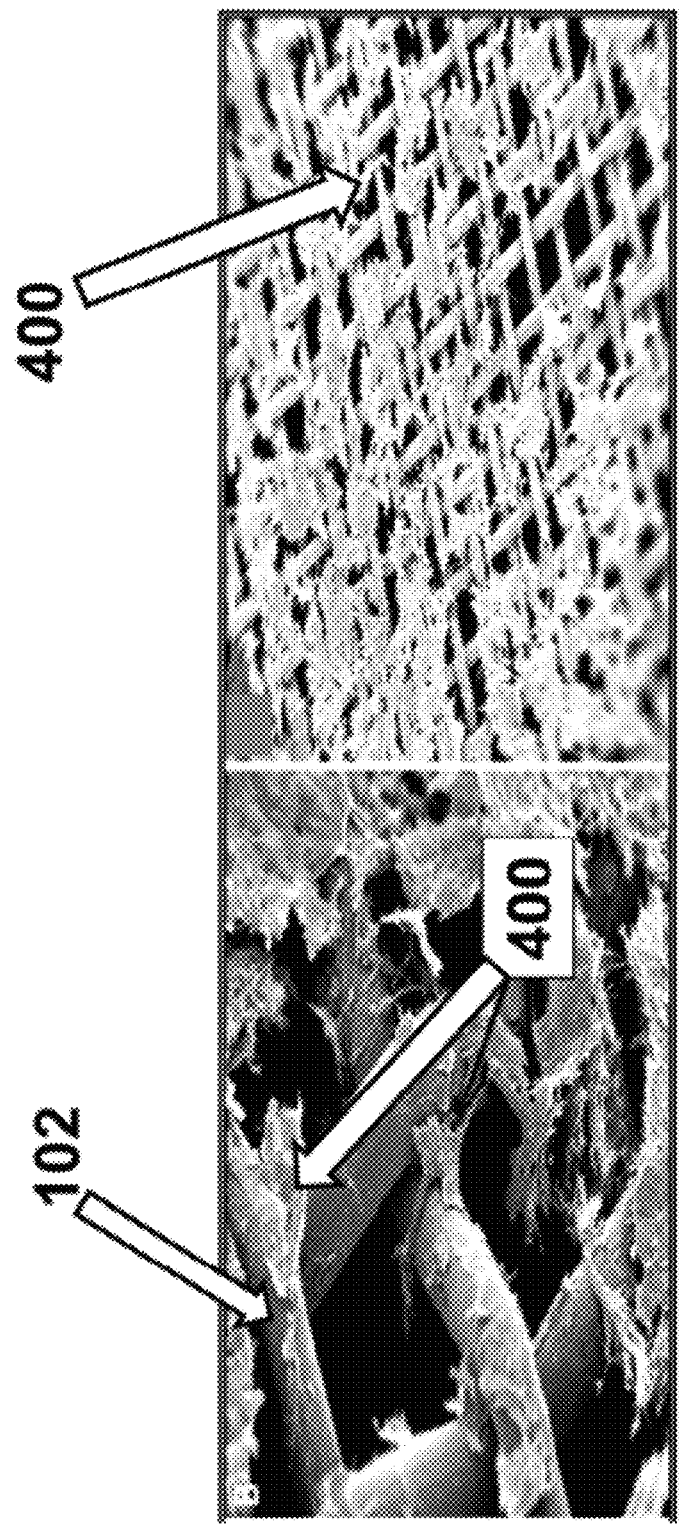

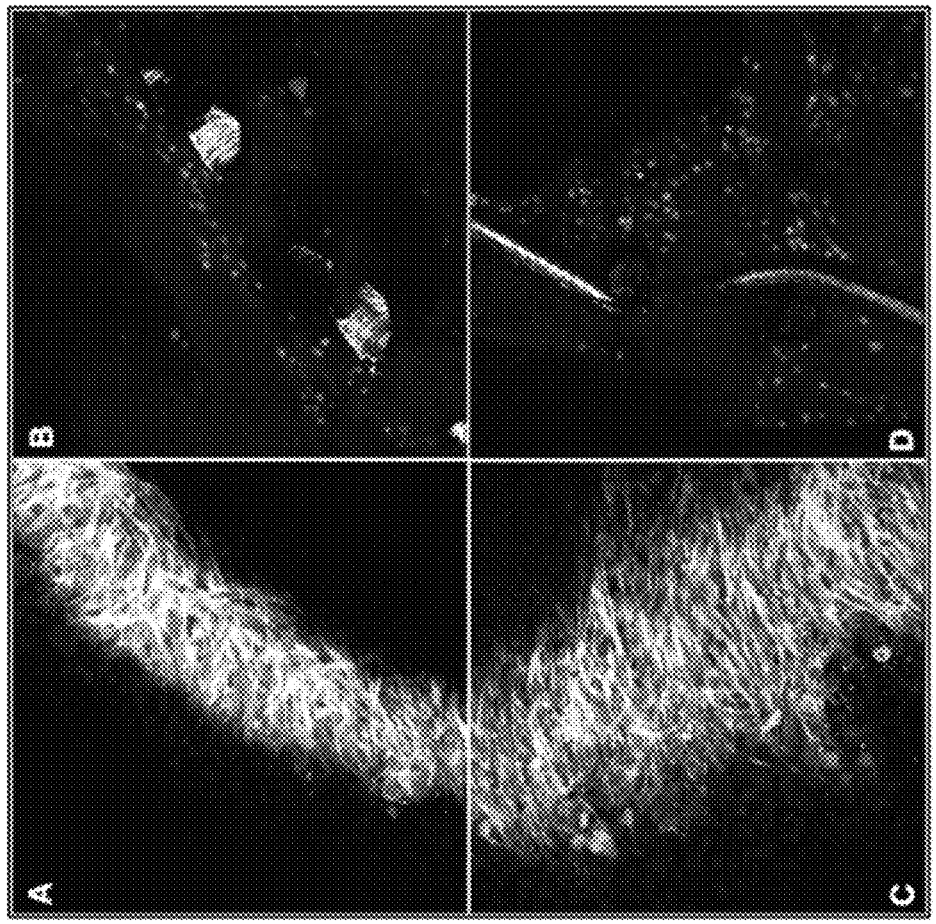

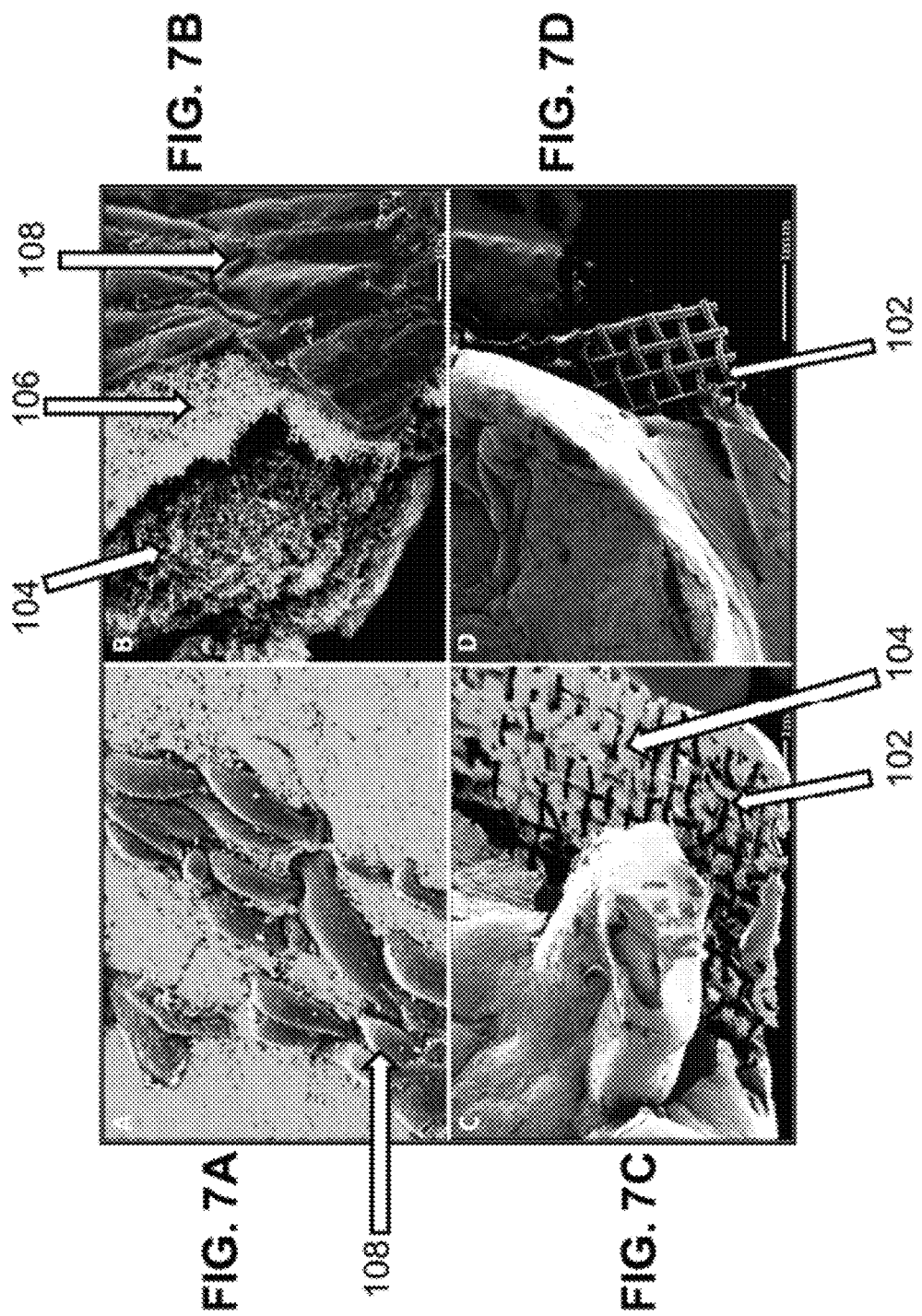

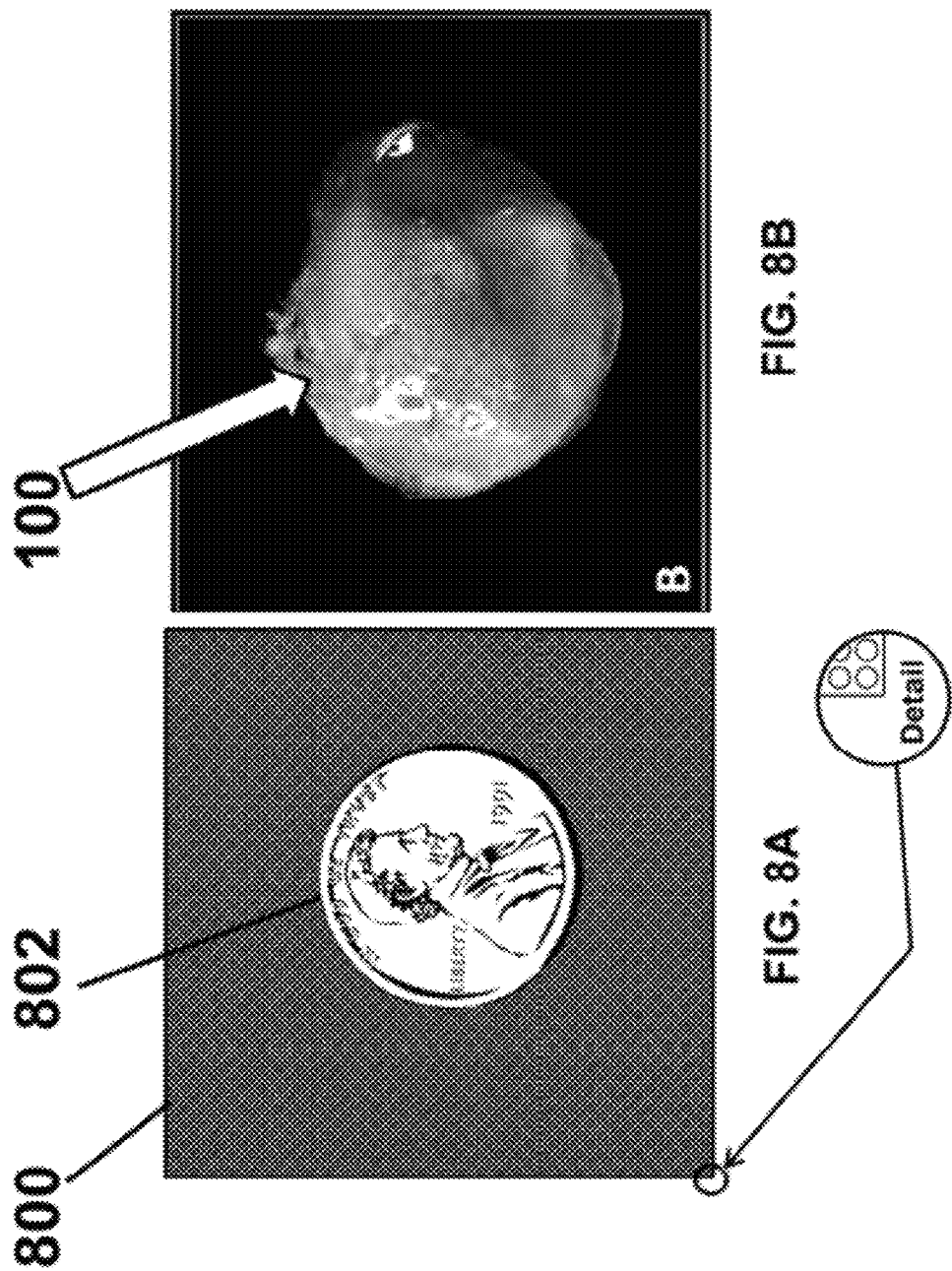

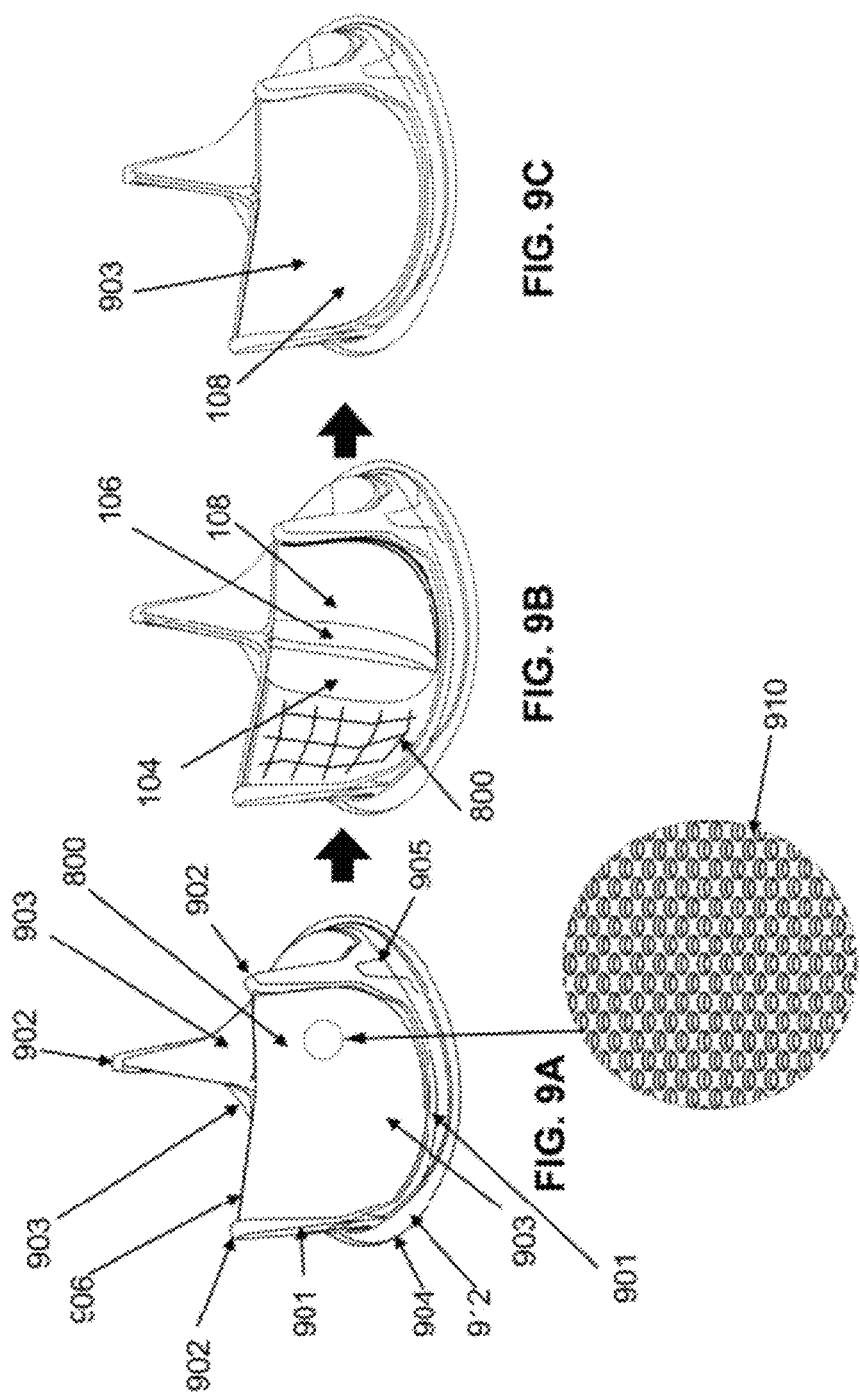

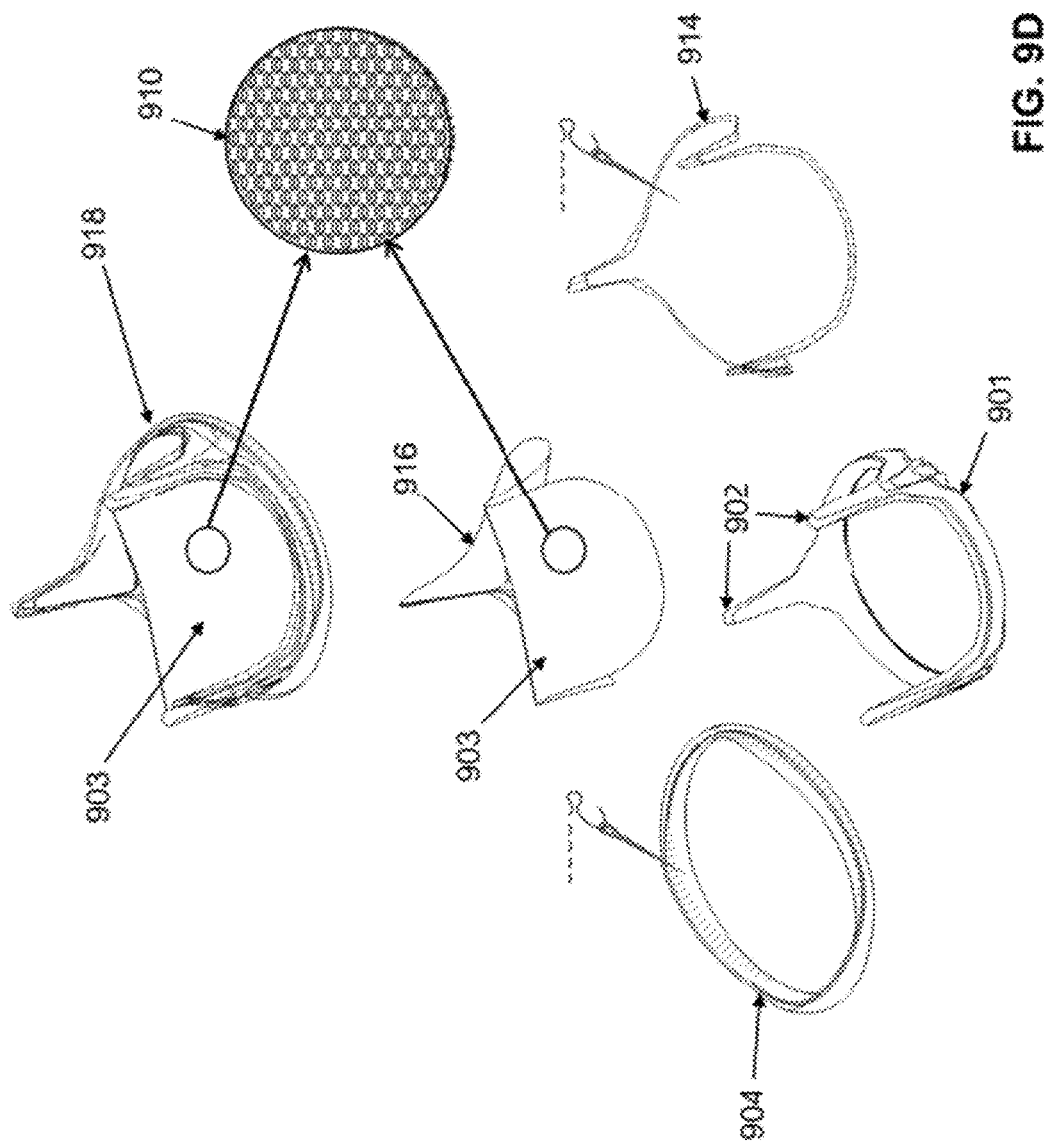

MESH ENCLOSED TISSUE CONSTRUCTS

PRIORITY CLAIM

This application is a non-provisional application of U.S. Provisional Application No. 61/466,882, entitled "A SELF-REGENERATIVE HYBRID TISSUE STRUCTURE FOR 3D FABRICATION OF HEART VALVES, BLOOD VESSELS AND OTHER CONSTRUCTS," filed on Mar. 23, 2011; AND U.S. Provisional Application No. 61/496,369, entitled, "HYBRID TISSUE ENGINEERED HEART VALVE," filed on Jun. 13, 2011; AND U.S. Provisional Application No. 61/540,330, entitled, "Scaffold for Fabrication of Engineered Heart Valves and Other Applications," filed on Sep. 28, 2011; AND U.S. Provisional Application No. 61/559,694, entitled, "METAL MESH SCAFFOLD FOR TISSUE ENGINEERING OF MEMBRANES," filed on Jan. 19, 2012.

BACKGROUND OF THE INVENTION (1) Technical Field

The invention pertains to methods for tissue engineering and, more particularly, to the fabrication of a scaffold that is composed of multi-layered tissue enclosed on a metal mesh.

(2) Description of Related Art

Engineering of the membrane-like tissue structures with ability to remodel and regenerate is currently an unresolved subject in the field of tissue engineering. Several attempts with minimal success have been made to create functional viable membrane tissues such as heart valve leaflet with the ability to grow, repair, and remodel. Shinoka et al. fabricated single leaflet heart valves by sequentially seeding ovine fibroblasts and endothelial cells on a bioabsorbable polymer composed of a polyglactin woven mesh surrounded by two non-woven polyglycolic acid mesh sheets. (See Shinoka, T., Breuer, C. K., Tanel, R. E., Zund, G., Miura, T., Ma, P. X., Langer, R., Vacanti, J. P., and Mayer J. E. Tissue engineering heart valves: Valve leafet replacement study in a lamb model. Ann Thorac Surg, 60, 13, 1995). Hoerstrup et al. fabricated a trileaflet heart valve using nonwoven polyglycolic acid mesh, a bioabsorbable polymer, sequentially seeded with ovine myofibroblasts and endothelial cells made using a pulse duplicator in vitro system. (See Hoerstrup, S. P., Sodian, R., Daebritz, S., Wang, J., Bacha, E. A., Martin, D. P., Moran, A. M., Guleserian, K. J., Sperling, J. S., Kaushal, S., Vacanti, J. P., Schoen, F. J., and Mayer, J. E. Jr. Functional living trileaflet heart valves grown in vitro. Circulation, 102, 44, 2000). Sodian et al. constructed trileaflet heart valve scaffolds fabricated from seeding ovine arterial vascular cells on a polyhydroxyoctanoate material. (See Sodian, R., Hoerstrup, S. P., Sperling, J. S., Daebritz, S., Martin, D. P., Moran, A. M., Kim, B. S., Schoen, F. J., Vacanti, J. P., and Mayer, J. E. Jr. Early in vivo experience with tissue-engineered trileafet heart valves. Circulation, 102, suppl III, 2000). Sutherland et al. created autologous semilunar heart valves in vitro using mesenchymal stems cells and a biodegradable scaffold made of polyglycolic acid and poly-L-lactic acid. (See Sutherland, F. W., Perry, T. E., Yu, Y., Sherwood, M. C., Rabkin, E., Masuda, Y., Garcia, A., McLellan, D. L., Engelmayr, G. C., Sacks, M. S., Schoen, F. J., and Mayer J. E. Jr. From stem cells to viable autologous semilunar heart valve. Circulation, 111, 2783, 2005). Drawbacks to the approaches described above include structural vulnerability, short term functionality, and limited mechanical properties of the membrane constructs.

Scaffolds are critical components of the engineered tissues that allow them to be formed in vitro and remain secure in vivo when implanted in a host. Several approaches have been taken to develop scaffolds for tissue membranes. The most widely used method involves biodegradable naturally-derived or synthetic polymers, where the polymer eventually degrades by normal metabolic activity, while the biological matrix is formed. To have viable tissue, the rate of scaffold degradation should be proportional to the rate of tissue formation to guarantee mechanical stability over time. The poor control of enzymatic degradation and low mechanical performance are two major limitations of naturally derived polymers. In contrast, synthetic polymers can be prepared precisely with respect to structure and function. However, most of them produce toxic chemicals when they degrade in vivo, and due to lack of receptor-binding ligands, they may not provide a good environment for adhesion and proliferation of cells.

Another option for creating scaffolds is to use decellularized xenogenic tissues, which has some advantages over polymeric materials. Decellularized tissues provide a unique scaffold, which is essentially composed of extracellular matrix (ECM) proteins that serve as an intrinsic template for cells. However, the process of decellularization cannot completely remove the trace of cells and their debris. These remnants not only increase the potential of an immunogenic reaction, but also result in increased tissue susceptibility to calcification.

Another, albeit less developed, strategy involves creating a scaffold with completely biological matrix components. This approach has advantages over using polymeric materials or decellularized xenogenic tissues. For example, large amounts can be produced from xenogenic sources, which can readily accommodate cellular ingrowth without cytotoxic degradation products. However, this strategy is restricted due to mechanical fragility of the scaffold and the low potentials for creating complex tissue structures.

Thus, a continuing need exists for a tissue construct that is strong enough to resist forces that exist inside a body, while possessing biocompatible surfaces.

SUMMARY OF THE INVENTION

The present invention is directed in a scaffold that is strong enough to resist forces that exist inside a body, while possessing biocompatible surfaces. The scaffold is formed of a layer of mesh (e.g., Stainless Steel or Nitinol) that is tightly enclosed by a multi-layer biological matrix. The biological matrix can include any desired number of layers, such a first layer (smooth muscle cells) formed directly on the metal mesh, a second layer (fibroblast/myofibroblast cells) formed on the first layer, and a third layer (endothelial cells) formed on the second layer.

The scaffold can be formed to operate as a variety of tissues, such as a heart valve or vascular graft. For example, the mesh and corresponding biological matrix can be formed as leaflets, such that the scaffold is operable as a tissue heart valve. In this aspect, the scaffold includes a flexible frame having a saddle-shaped base with at least two upstanding posts, with the leaflets each having a peripheral free portion extending between the posts and a fixed portion attached with the base.

In another aspect, the scaffold is formed as a vascular graft. In this aspect, the layer of mesh is a tubular wire mesh, with the biological matrix formed around the mesh to completely conceal the mesh therein.

As can be appreciated by one skilled in the art, the present invention is also directed to the method of forming the scaffold described herein. The method includes a plurality of acts, such as preparing a layer of mesh and growing a biological matrix around the layer of mesh such that the biological matrix tightly encloses the layer of mesh.

In another aspect, the act of preparing the layer of mesh further comprises a preparation technique, or any combination thereof, selected from a group consisting of polishing the layer of mesh; acid washing the layer of mesh; ultrasonic clean washing the layer of mesh; and glow discharging the layer of mesh.

Additionally, the act of preparing the layer of mesh further comprises an act of ion beam surface modification to provide a smooth surface and ensure the biocompatibility and enhanced cell attachment.

In yet another aspect, growing a biological matrix around the layer of mesh further comprises an act of providing collagen as an additive to coat the layer of mesh to ensure development of an interconnected pore network.

In another aspect, wherein growing a biological matrix around the layer of mesh further comprises an act of sequentially seeding three different types of cells on the layer of mesh. In sequentially seeding three different types of cells on the layer of mesh, the three different types of cells are smooth muscle cells, fibroblast/myofibroblast cells, and endothelial cells. Further, protein, including TGF-β1, can be added to the collagen in each layer. Thus, as described above, the present invention is directed to a scaffold and various methods for forming such a scaffold.

BRIEF DESCRIPTION OF THE DRAWINGS

The objects, features and advantages of the present invention will be apparent from the following detailed descriptions of the preferred aspect of the invention in conjunction with reference to the following drawings where:

FIG. 3A is an image of a stainless steel mesh with a surface area of about 1 cm$^2$;

FIG. 3B is a view of the engineered tissue after three months of cell culture;

FIG. 4A is a scanning electron micrograph of the first layer on the mesh showing that smooth muscle cells are attached over the mesh;

FIG. 4B is a expanded view of FIG. 4A;

FIG. 6A shows a top view of cell culture without addition of TGF-β;

FIG. 6B shows a top view of cell culture without addition of TGF-β;

FIG. 6C shows the top view of the cell culture with TGF-β added to the cell culture;

FIG. 6D shows the top view of the cell culture with TGF-β added to the cell culture;

FIG. 7A is a scanning electron microscopy image that show layers of tissue tightly enclosing the stainless steel mesh;

FIG. 7B is a scanning electron microscopy image that show three layers of tissue tightly enclosing the stainless steel mesh;

FIG. 7C is a scanning electron microscopy image that show three layers of tissue tightly enclosing the stainless steel mesh;

FIG. 7D is a scanning electron microscopy image that show three layers of tissue tightly enclosing the stainless steel mesh;

FIG. 8A is an illustration depicting a size comparison of a one-centimeter by one-centimeter Nitinol mesh in relation to a United States Penny;

FIG. 8B shows the engineered tissue on Nitinol mesh after the months of cell culture;

FIG. 9A is an illustration of a heart valve depicting the Nitinol mesh scaffolding;

FIG. 9B is an illustration of a heart valve with heart leaflets that are made of tissue described in this application;

FIG. 9C is an illustration of a heart valve with heart leaflets that are made of tissue described in this application;

FIG. 9D is an illustration depicting schematic parts of a tri-leaflet scaffold that can be used as a heart valve;

DETAILED DESCRIPTION OF THE INVENTION

Figure 1:
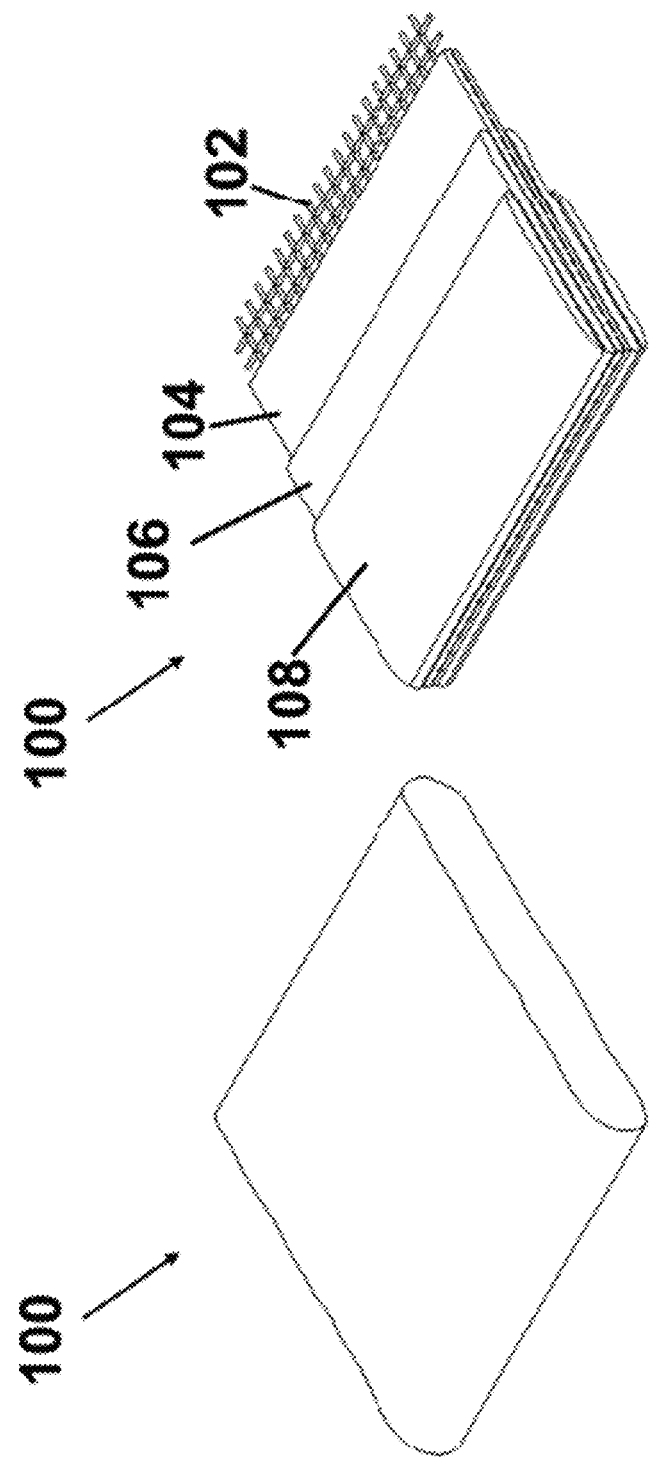
FIG. 1A shows a representation of a scaffold of one aspect of the present invention.
FIG. 1B is a diagram showing the three layers of cells of a scaffold that mimic heart valve tissue structure of one aspect of the present invention.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications, and equivalents, which may be included with the spirit and scope of the invention as defined by the appended claims. Furthermore, in the following detailed description of embodiments of the present invention, numerous specific details are set forth in order to provide thorough understanding of the present invention. However, it will be recognized by one of ordinary skill in the art that the present invention may be practiced without these specific details. In other instances, well-known methods, procedures, and components have not been described in detail as not to unnecessarily obscure aspects of the embodiments of the present invention.

As noted above and as shown in FIG. 1A, the present invention is directed to a scaffold 100 that is composed of multi-layered tissue enclosed on a metal mesh. This is further illustrated in FIG. 1B, which illustrates that the scaffold 100 is made of an extra layer of metal mesh 102 enclosed by a biological matrix, such as layers (e.g., three layers) of cells (e.g., different cell types). It should be understood that while the present invention is described as scaffold 100 that includes three layers of different cell types, it is not intended to be limited thereto as the scaffold 100 can be formed with a single layer, or any suitable number of layers, and, further, with a single or different cell types. Additionally, while the mesh 102 is described as being covered with biological materials or a biological matrix, the invention is not limited thereto as the mesh 102 can also be enclosed by synthetic materials that are known to one skilled in the art (such as polymers, etc.) As a non-limiting example, the synthetic material can be molded onto the mesh.

However, desirably, the three layers of biological materials include a first layer 104 of smooth muscle cells. The second layer 106 may be composed of fibroblast and myofibroblast cells and the third layer 108 (which can is the outer layer) may comprise of endothelial cells. These three layers wrap around the metal mesh 102 in three-dimensions so that each layer fully envelopes the metal mesh 102. This approach is intended to retain all the advantages of using biological scaffolds while developing a strong extracellular matrix (ECM) backbone composed of the mesh 102 that can withstand various types of loads after implantation inside the body. Additionally, such a mesh pattern ensures structure integration of the formed tissue and allows cells and ECM components on both sides of the mesh 102 to interact with each other. The formed tissue is intended to be biomechanically resilient against the physiological stresses inside the body. In one aspect, the scaffold 100 is a living tissue, able to continually remodel and mature in vitro and in vivo. For example, the scaffold 100 has living tissue (as described below) that can continue to grow and mature, with the mesh 102 becoming biologically active when implanted in-vivo.

In one aspect, the three layers of cells of the scaffold 100 may mimic the heart valve structure. These three layers mimic ventricularis, spongiosa and fibrosa layers of a heart valve leaflet. This type of scaffold can be used in any membrane tissue fabrication, such as heart valve leaflets, vascular grafts, etc.

Figure 2:
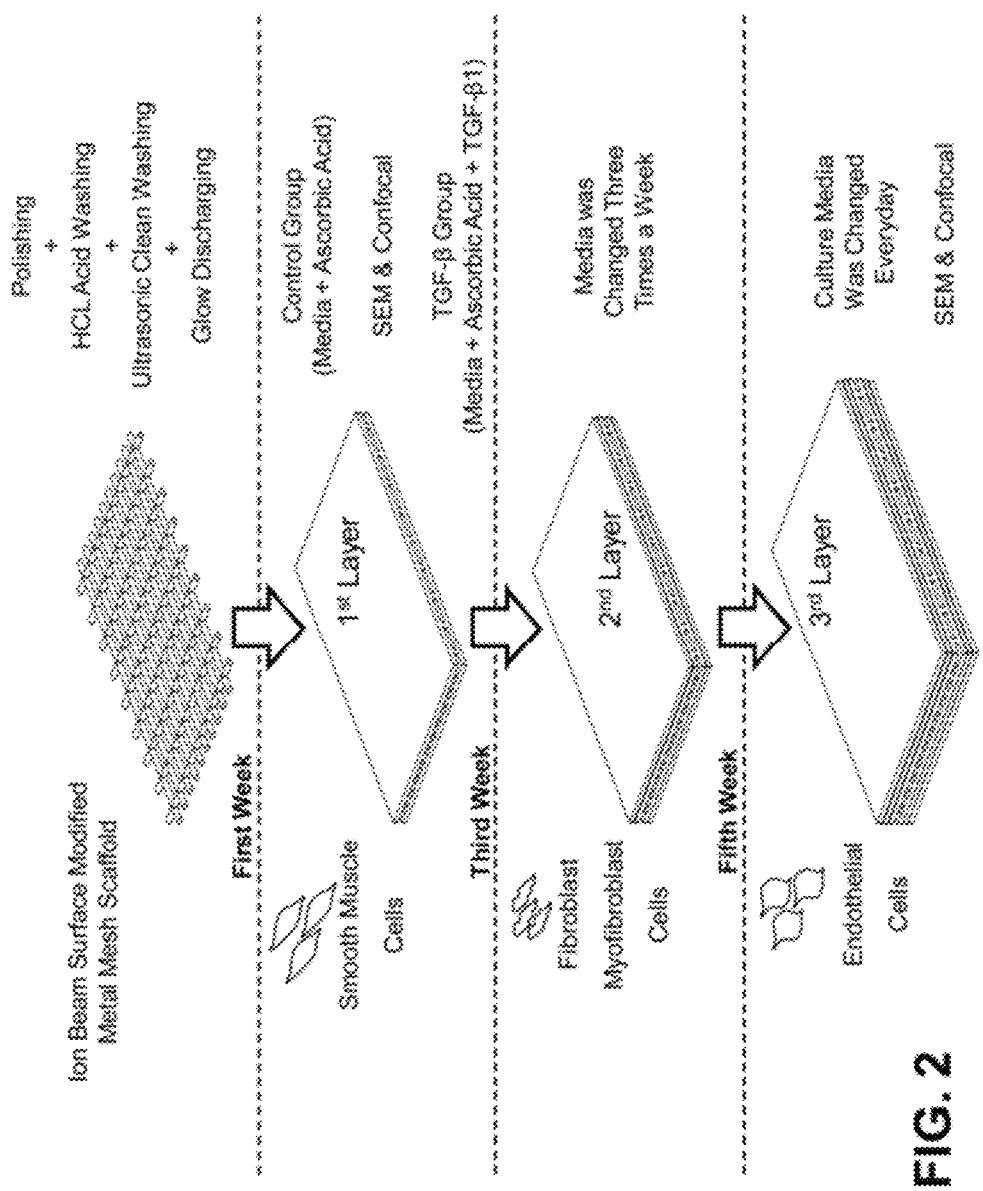
FIG. 2 is a schematic showing the steps in the three-dimensional (3D) cell culture method to develop a tissue.

While the present invention is directed to a unique hybrid scaffold 100 as shown in FIGS. 1A and 1B, the present invention also includes the method of making the novel scaffold (made of an extra layer of metal mesh enclosed by three layers of different cell types). For example, FIG. 2 shows a schematic diagram of a method for producing the multilayered tissue. Through the three-dimensional cell culture technique detailed in this application, all layers of the cells were seeded on rectangular-shaped Stainless Steel meshes to produce ECM or connective tissue.

The method of making the multilayered tissue is as follows. The first step in creating the scaffold is preparation of the metal mesh scaffold. The metal mesh is any suitable material that can operate as scaffolding for a tissue. As a non-limiting example, the metal mesh may be a flat mesh of T316 Stainless Steel woven from 0.0037" round wires, targeting at 80 end per inch (EPI)×80 pick per inch (PPI) that possesses an opening size of 0.0088". A non-limiting example of such a mesh is that sold by TWP, Inc., located at 2831 Tenth Street, Berkeley, Calif. 94710 USA. The metal mesh was heated at 520° C. for 5 min, followed by water quenching. The oxidized film was removed at multiple stages; by polishing the surface, using hydrochloric acid wash, ultrasonic cleaning wash in ethanol for 15 min and glow discharging for 40 seconds. Finally, the mesh was cut into pieces with area of one square centimeter to be used for cell culture.

After the metal was cleaned and cut into pieces, an ion beam surface modification method was used to get a smooth surface and ensure the biocompatibility and enhanced cell attachment for the Stainless Steel meshes. The meshes were mechanically polished with wetted metallographic polishing high-grade Silicon Carbide (SiC) papers. Afterward, the meshes were acid-washed, degreased in an ultrasonic vibro-bath, and rinsed with distilled water. Prior to cell culture, the samples were irradiated by $He^+$ ion beam at energy of 150 keV with fluences of $1\times10^{14}$ ions/$cm^2$.

In one aspect, the growth of the tissue may be aided by the addition of growth factors and materials. For example, a mixture containing bovine and rat tail collagen may be used to coat the mesh to ensure development of an interconnected pore network, which is essential for cell growth, nutrient supply, and removal of metabolic waste products. In addition, the culture media may be supplemented with additives, including, but not limited to, ascorbic acid to promote matrix production. Moreover, proteins (cytokines), including TGF-$\beta 1$, may be added to the collagen gels in each layer to increase the rate of extracellular matrix production. For the biological part of the scaffold any collagen type by itself or in mixture as well as the other biological scaffold such as fibrin or even synthetic scaffolds can be used. Growth factors depending on the target tissue and the cells that have been used can be different, such as vascular endothelial growth factor (VEGF) if endothelial progenitor cells are used instead of endothelial cells.

After the mesh has been prepared, the three-dimensional tissue scaffold was constructed by sequential seeding of three different types of cells on the metal mesh. As a non-limiting example, three different cell types were isolated and used for preliminary assay, as follows: smooth muscle cells and fibroblast and myofibroblast cells to fulfill the role of valvular interstitial cells (VICs) and endothelial cells to act as the valvular endothelial cells. The basal media for culturing cells contained DMEM (e.g., Dulbecco's Modified Eagle Medium, Gibco, produced by Invitrogen Corporation, located at 1600 Faraday Ave., Carlsbad, Calif. 92006, USA), 10% fetal bovine serum (HyClone, Rockford, Ill.), 1% penicillin/streptomycin (Gibco, Carlsbad, Calif.) and 1% L-glutamine (Gibco, Carlsbad, Calif.), with appropriate growth factors added to it for enhancement of growth and proliferation. Cultured cells were fed every two to three days, and split 1 to 3 at confluence. Cells were used on the passages 3 to 5 for the experiment.

Each mesh was coated with a mixture of bovine and rat tail collagen (Gibco, Carlsbad, Calif.) in a tissue culture hood with an aligned appearance. The liquid collagen mixture was neutralized using NaOH. Cell-seeded collagen constructs were prepared by first casting an acellular collagen solution and then adding a total of $3\times10^6$ cells for each cell type to it, before the collagen had set. After placing the Stainless Steel meshes among the solutions, the constructs were incubated at 37° C. in a 5% $CO_2$ humidified incubator for polymerization. This method ensures that collagen constructs have uniform cell density ($3\times10^6$ cells/$cm^2$) after gel formation. The tissue constructs were cultured at 37° C. with replacement of culture media every two days. To achieve a phenotype similar to the natural valve leaflets in-vivo, the cells in the next layers were plated over the constructs at time intervals of two weeks and the next layer was constructed around the deeper layer in a similar method that has been described in the beginning of this paragraph. The media was also supplemented with ascorbic acid (e.g., produced by Sigma-Aldrich Inc., located at 3050 Spruce Street, St. Louis, Mo. 63103, USA) as an additive to promote matrix production. To increase the rate of extracellular matrix production, 10 ng/ml of TGF-$\beta 1$ (e.g., produced by R&D Systems Inc., located at 614 McKinley Place Northeast, Minneapolis, Minn. 55413, USA) was added to the collagen gels in each layer. These cultures were later on compared to the control group with no TGF-$\beta$ supplementation.

In one aspect, the tissue may be suitable for applications in which strong composition of the membrane is essential, including but not limited to, heart valves and vascular grafts. For further understanding, FIGS. 3A and 3B provide images that depict the scale and size of the mesh and corresponding tissue. For example, FIG. 3A is an image of a stainless steel mesh 102 with a surface area of about one square centimeter Additionally, FIG. 3B is a macroscopic view of the engineered tissue 100 after three months of cell culture. The outer surface shown in FIG. 3B is the endothelial layer or the third layer. Seeding the third layer completely concealed the mesh 102 and formed a smooth, confluent surface around the construct. Although the third layer concealed the mesh 102, the metallic mesh 102 can still be seen inside the tissue.

FIG. 4A and FIG. 4B are scanning electron micrographs (SEM) images of the first layer of cells. FIG. 4A shows the smooth muscle cells 400 as being attached over the mesh 102. FIG. 4B shows the first layer of tissue (i.e., the smooth muscle cells 400) compacted during the culture period, which confirmed the expression of alpha-SMA, as its expression.

Figures 5A, 5B:
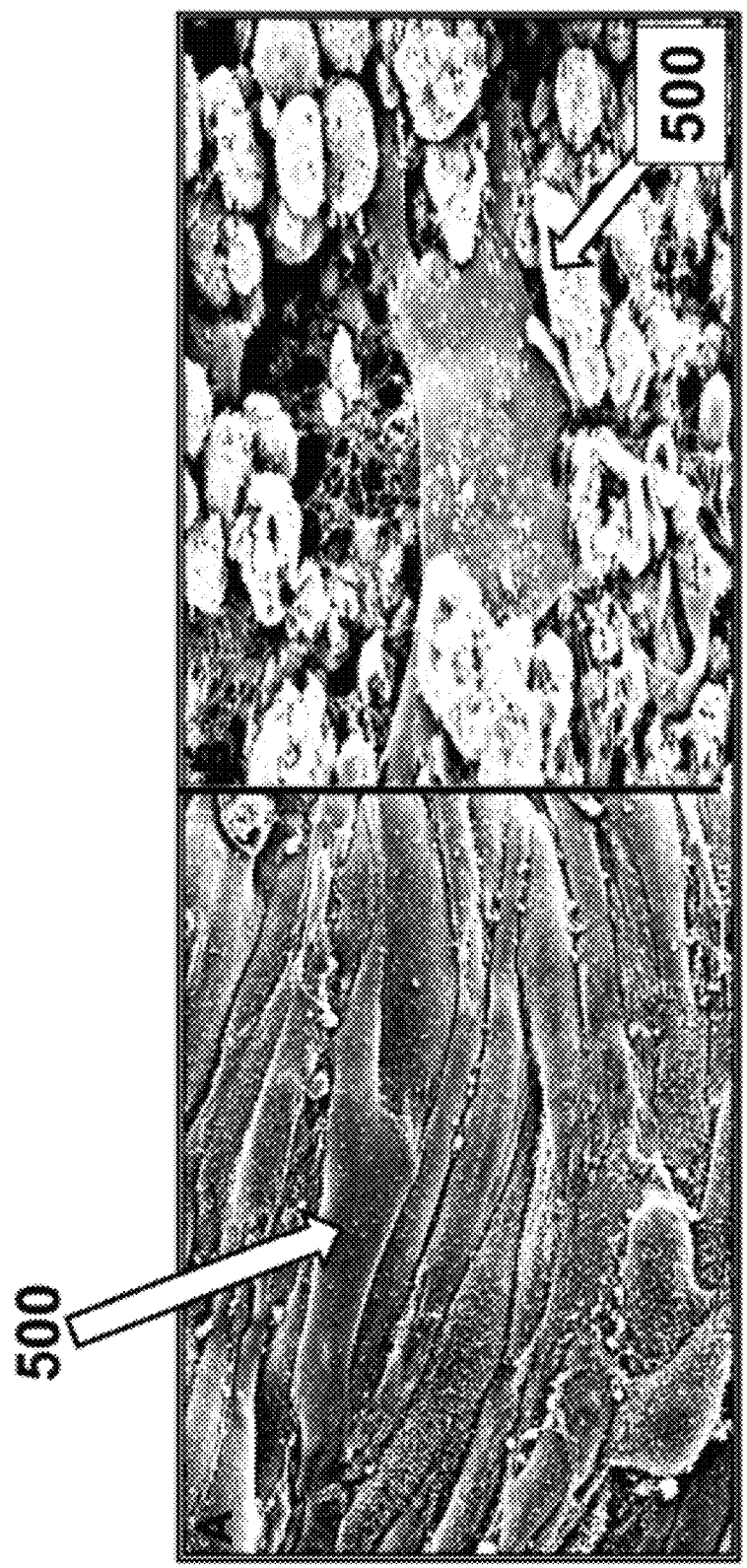
FIG. 5A is a scanning electron microscropy image taken after culturing the second layer of cells containing fibroblasts and myofibroblasts.
FIG. 5B shows the formation of extracellular matrix and a layer of cells formed on the metal mesh, the black arrow indicates a single fibroblast cell.

FIG. 5A is a top-view of the SEM image taken after culturing the second layer of cells containing fibroblasts/myofibroblasts. Formation of ECM and a confluent layer around the construct are visible. Alternatively, FIG. 5B shows a side-view of the SEM image. The arrow in FIG. 5B indicates a single fibroblast cell 500. Both FIG. 5A and FIG. 5B show fibroblast cells 500 in the second layer. Addition of TGF-β increased the number of cells with either fibroblasts or myofibroblasts in the second layer.

FIG. 6A through FIG. 6D show confocal microscopy images of the cell culture at the end of the eighth week, with and without addition of TGF-β. FIG. 6A shows the control group from a top-view, without TGF-β added. FIG. 6B shows the control group from a side-view without TGF-β added. Alternatively, FIG. 6C is a top-view image of the cell culture with TGF-β added to the cell culture. FIG. 6D is a side-view image, showing the cell culture with TGF-β added to the cell culture. As shown between FIGS. 6A through 6D, greater extracellular matrix deposition is observed when TGF-β is added, in comparison to control groups. DAPI (i.e., 4',6-Diamidino-2-Phenylindole, Dihydrochloride) staining of nuclei in the construct shows that the number of cells at the surface of the mesh increased progressively in TGF-β groups, and the groups treated with TGF-β eventually formed a thicker tissue around the mesh.

FIGS. 7A through 7D show SEM images taken after eight weeks, depicting the three layers of tissue tightly enclosing the stainless steel mesh. FIG. 7A shows the endothelial surface layer, the smooth structures 108, covering the construct in a confluent manner. FIG. 7B shows that after eight weeks, the tissue shows three different cell layers in sequence, 108 is the surface endothelial layer, 106 is the middle fibroblast and myofibroblast layer, and 104 is the base layer of smooth muscle cells. FIG. 7C and FIG. 7D show that the mesh 102 is tightly integrated with the tissue membrane, with FIG. 7C further illustrating that the cells 104 are penetrating through the mesh 102 opening holes. It can be observed that adding the second and the third layers improves production of the ECM (mainly collagen and glycosaminoglycans) that covers the mesh, forming a confluent smooth surface with endothelial cell lining in both experimental groups.

As noted above, the metal mesh is any suitable material that can operate as scaffolding for a tissue. Further, the mesh can be in any form, non-limiting examples of which include being braided or flat (e.g., the mesh is fabricated as sheet of punched wire mesh or with a woven pattern). In another aspect, a Nitinol metal mesh scaffold may be used instead of stainless steel metal mesh for the scaffold. For scale comparison, FIG. 8A shows multiple sheets of one centimeter by one centimeter Nitinol mesh 800 in relation to a United States one cent coin 802. In production of the tissue, the Nitinol metal mesh 800 is etched with acid in the same process used for the Stainless Steel metal mesh. In this non-limiting example, the mesh 800 is made of a superelastic Nitinol sheet with the thickness of 76 microns etched as a network of holes with 240 microns diameter and the central distance of 320 microns. For the heart valve leaflet application, a sheet that is 25 microns thick is used, which provides the desired elastic recoil of the leaflets. In this aspect, the mesh 800 is cut to the shape of a heart valve leaflet. The Nitinol mesh is seeded with cells in the same manner as the described for the Stainless Steel mesh. An example of the resulting scaffold 100 that is grown for 3 months is shown in FIG. 8B.

As noted above, the scaffold of the present invention can be incorporated into any suitable tissue based item, a non-limiting example of which includes a vascular graft. As another non-limiting example and as shown in FIGS. 9A through 9C, the scaffold may be incorporated into a tissue heart valve that mimicks the natural heart valve. The tissue heart valve comprises a flexible frame having a saddle-shaped base 901 and at least two upstanding posts 902 (or three as depicted), which divide the base into at least two portions (or three as depicted), together with tissue leaflets 903 formed from the tissue described in this application. The posts 902 can be formed at opposite ends of a diameter of an undistorted base or, as depicted three (or more) posts 902 are placed at regular intervals around the base.

The tissue leaflets 903 each having a periphery consisting of a free portion 906 extending between the tips of posts 902 and a fixed portion secured, sealed or sutured to corresponding sides of the posts 902 and the adjacent portion of the base 901. The leaflets 903 are made of a mesh material, such as but not limited to superelastic Nitinol mesh (or Stainless Steel or any other suitable mesh material). The superelastic mesh acts as a structure that defines the shape of the leaflets 903 and can be a structure, such as but not limited to a mesh with arranged or unarranged holes. The mesh can be fabricated, such as but not limited to a sheet of punched wire mesh or with a woven pattern.

To use the heart valve shown in FIGS. 9A through 9C, the saddle-shaped base 901 is attached to the circumference of the auriculoventricular orifice, preferably through an intermediate suture ring 904, whereby the base can deform from a substantially circular shape to the shape of the orifice simultaneously, as is the case with the natural heart valve. In a valve replacement, the posts 902 may be disposed at regular intervals round the undistorted base, or at other intervals as needed, for example, by the anatomical requirements of coronary ostia in aortic valve replacement.

The flexible frame (i.e., saddle-shaped base 901 and at least two upstanding posts 902) is formed of any suitably flexible yet durable material. As a non-limiting example, the flexible frame is desirably formed of Elgiloy covered with a woven polyester cloth 912 (such as but not limited to Dacron cloth, or any other suitable covering material), with the differential flexibility afforded by differing thicknesses of the frame material to either side of the posts and/or differing thicknesses of Eligiloy at each portion of the posts. It is designed to be compliant at the orifice and commissures to reduce the closing loading shocks at the commissure tips and free margin of the leaflets. The suture ring 904 can contain inserts of silicone rubber and non-woven polyester. At least two contrasting marking sutures 905 are located on the suture ring 904. The marking sutures 905 are intended to aid in the proper orientation for implanting the prothesis. The posts 902 desirably merge at each side into the respective arcuate portions of the saddle-shaped base 901, with the merging preferably being by way of a continuous curve from the rounded tip of one post 902 to the rounded tip of the other post 902.

For example in a tri-leaflet valve, the shape of each leaflet 903 preferably corresponds to a portion of a surface of a cone, which portion is defined by the intersections on the conical surface of three flat planes with sixty degree angles together. The three flat panes having peripheries on the conical surface corresponding in length respectively to the circumference of the saddle-shaped base and the distance between the tips of the posts of the frame. A forth intersection is included on the conical surface of a curved plane that is concave towards the apex of the cone and intersects the three mentioned flat planes at opposite sides of the cone. The spacing of the flat planes and the curvature of the curved plane are such that the development of the curved plane on the conical surface matches in length and curvature a continuously blending of the curve of one arcuate portion of the saddle-shaped base and the adjacent sides of the posts, so that no moulding or stress-fixing of the leaflet material is required.

For further understanding of the scaffold nature of the heart valve, FIG. 9A depicts the heart valve with the mesh (such as Nitinol mesh 800) that is the underlying base structure of the leaflets 903. Specifically, FIG. 9A illustrates the heart valve and its scaffold without the biological matrix. FIG. 9A includes an enlarged view 910 of the mesh 800 to illustrate a non-limiting example of a mesh pattern and the holes therethrough. Further, as shown in FIG. 9B, the three layers are grown on top of the Nitinol mesh 800. Specifically, shown is the first layer 104 of smooth muscle cells, the second layer 106 of fibroblast and myofibroblast cells and the third layer 108 of endothelial cells. Finally, FIG. 9C illustrates a resulting heart valve, where the outer layer of each leaflet 903 is the third layer 108 (or endothelial cells).

For further understanding of a suitable base structure, FIG. 9D illustrates components of the heart valve as depicted in FIG. 9A. Shown in FIG. 9D is the flexible frame that includes the saddle-shaped base 901 and at least two upstanding posts 902. The suture ring 904 is also depicted in FIG. 9D, along with the suture material 914. Further, the leaflets 903 are shown, including an enlarged view 910 of the mesh to illustrate an example of the mesh pattern.

Figure 9E:
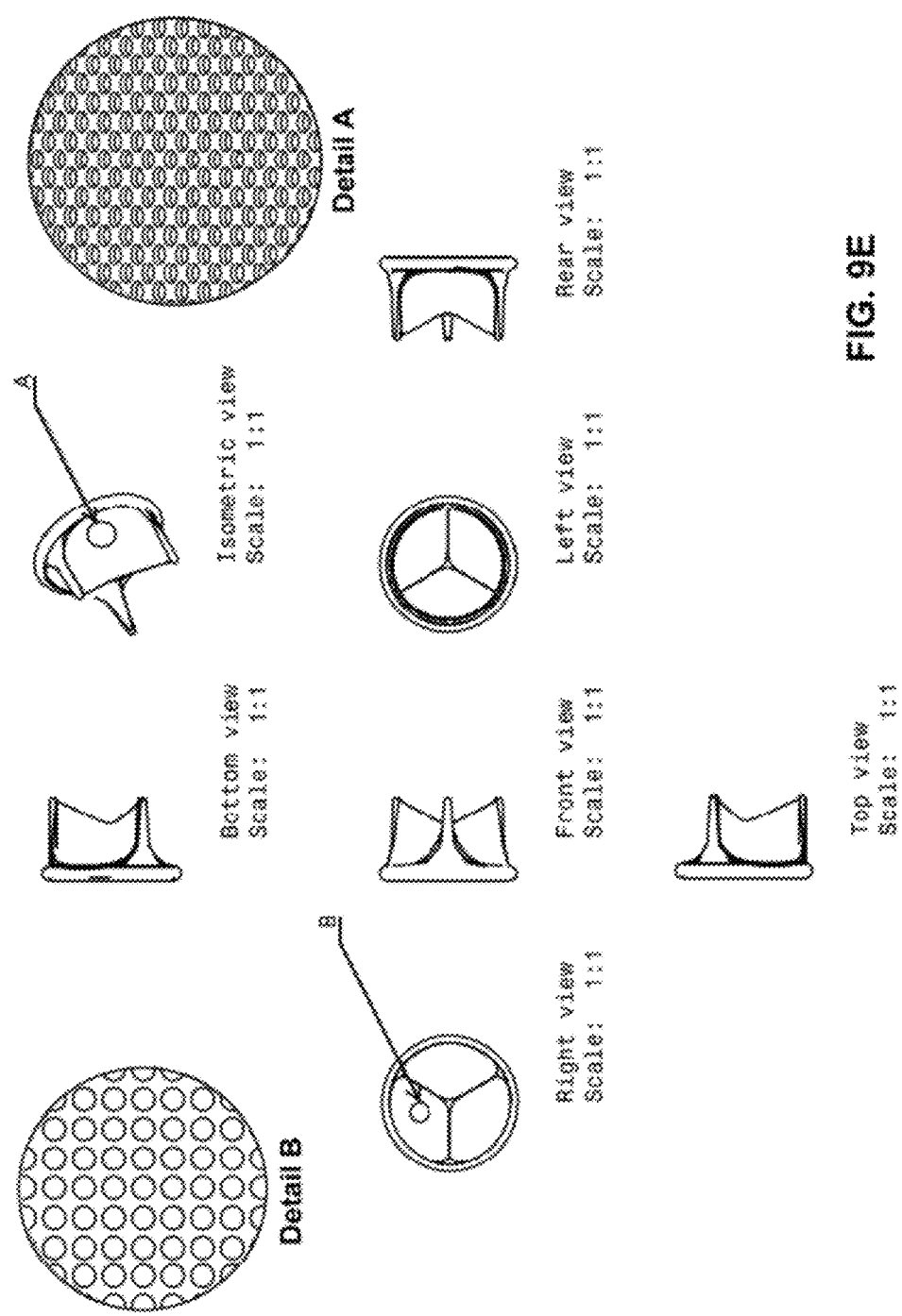
FIG. 9E is an illustration that includes various view-point illustrations of the heart valve.
Figure 9F:
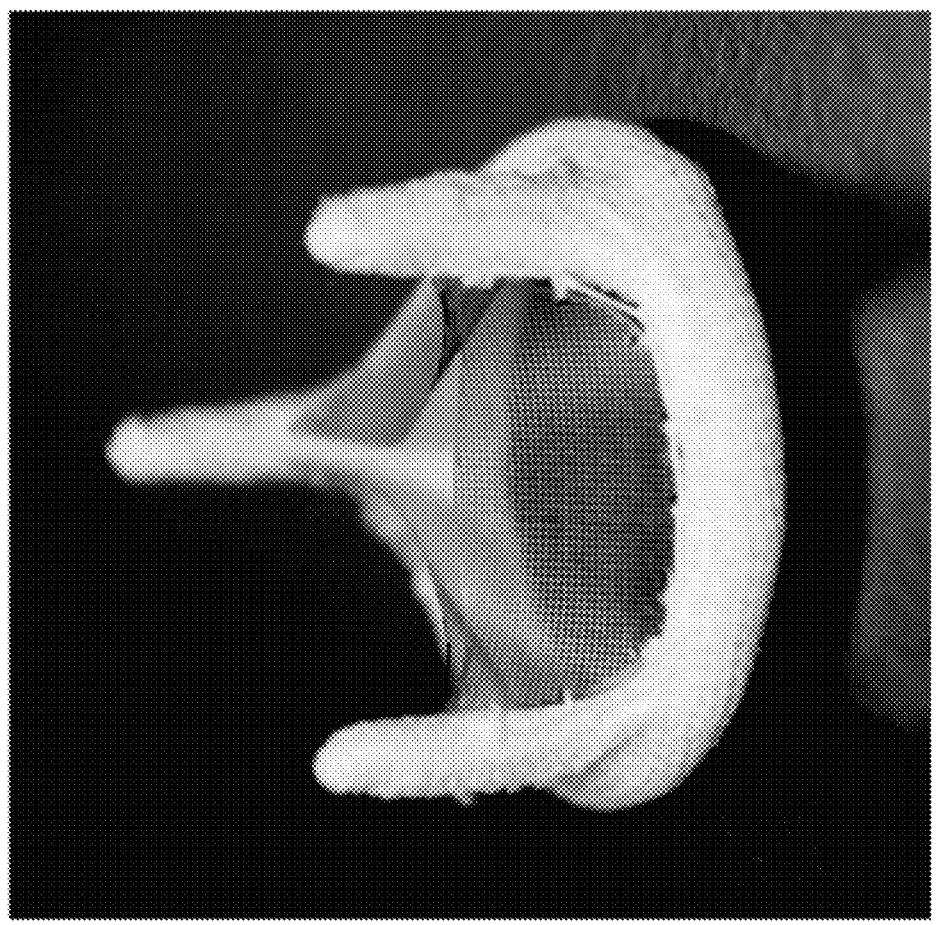
FIG. 9F is an image of the tri-leaflet scaffold that is depicted in FIGS. 9A and 9D.

As shown, the leaflets 903 can be attached together to form a dimensionally stable and consistent coapting leaflet subassembly 916 when subjected to physiological pressures. Then each of the leaflets 903 of the subassembly 916 is aligned with and individually sewn to the frame (i.e., the saddle-shaped base 901 and posts 902), typically from one commissure tip (i.e., post 902), uniformly around the leaflet 903 cusp perimeter, to the tip of an adjacent commissure tip (post 902). The frame (base 901 and 902) is usually covered with cloth but can alternatively be covered with biologic tissue. The sewed sutures 914 act like similarly aligned staples, all of which equally take toe loading force acting along the entire cusp of each of the pre-aligned leaflets 903. The resulting structural assembly (i.e., the heart valve 918 depicted at the top of FIG. 9D and also shown in FIG. 9A) thereby formed reduces stress and potential fatigue at the leaflet suture interface by distributing stress evenly over the entire leaflet cusp from commissure to commissure. Thus, unlike some bioprosthetic valves wherein leaflets are attached individually and the peripheral stitching of the cusps terminates before the tips of the commissures, producing a potential stress point, the produced valve assembly has uniform stitching from commissure tip to commissure tip and consistently aligned coapting leaflet mating edges. This is further illustrated in FIG. 9E, which provides various view-point illustrations of the tri-leaflet heart valve to clearly illustrate the shape of the valve assembly (i.e., tri-leaflet heart valve) and its leaflet mating edges. Finally and for further illustration, FIG. 9F provides an illustration of the tri-leaflet scaffold that is depicted in FIGS. 9A and 9D.

Figure 10A:
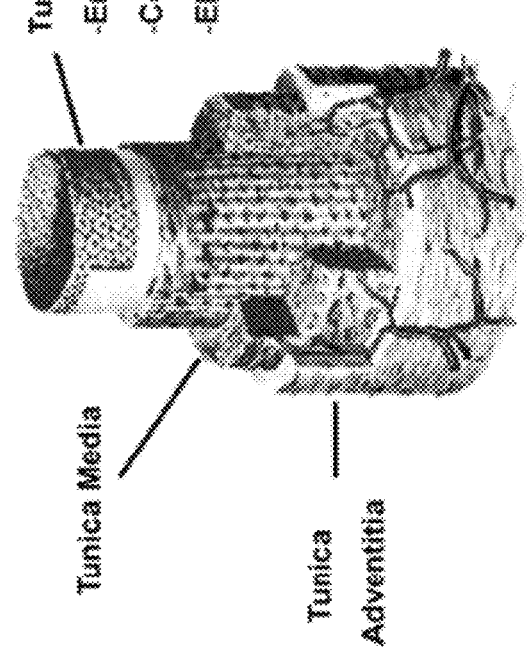
FIG. 10A is a schematic representation of a blood vessel.
Figure 10B:
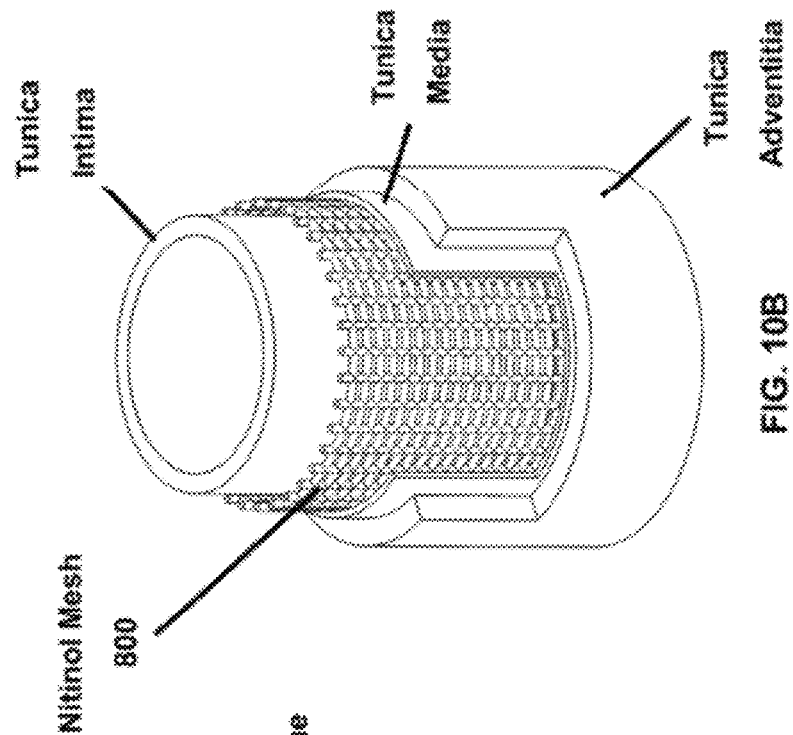
FIG. 10B is a schematic representation of a blood vessel formed from the tissue described in this application.

FIG. 10A and FIG. 10B provide yet another example of a tissue based item that can be adapted or formed to incorporate the scaffold. For example, FIG. 10A is a schematic representation of a blood vessel, depicting the various components of an actual blood vessel. Alternatively, FIG. 10B illustrates the scaffold formed as a blood vessel. As shown, the scaffold in this example includes the base Nitinol mesh 800 that is provided in a tubular wire mesh form to mimic the shape of a blood vessel. The corresponding tissue is grown around the Nitinol mesh 800. Thus, as can be appreciated, the present invention enables for the generation of a variety of scaffolds that are strong enough to resist forces that exist inside a body, while possessing biocompatible surfaces.

What is claimed is:

1. A method for forming a scaffold, comprising:
preparing a layer of mesh having a first side and a second side, the layer of mesh being either a woven wire metal mesh or a flat metal sheet that is acid-etched, such that the layer of mesh comprises a network of holes passing directly through the mesh from the first side to the second side, and
growing a biological matrix around the layer of mesh such that the biological matrix comprises at least three layers of cells at each side of the mesh enclosing the layer of mesh, such that the at least three layers of cells on the first side interacts with the at least three layers of cells on the second side through the network of holes to provide for structure integration, wherein the at least three layers of cells at each side of the mesh comprise a first layer formed directly on the metal mesh, a second layer formed on the first layer, and a third layer formed on the second layer, such that the first layer of cells is a smooth muscle cell layer, the second layer of cells is a fibroblast/myofibroblast cell layer, and the third layer is an endothelial cell layer.

2. The method of claim 1, wherein the mesh is formed of stainless steel wires, and wherein said preparing the layer of mesh further comprises a preparation technique, or any combination thereof, selected from the group consisting of:
polishing the layer of mesh;
acid washing the layer of mesh;
ultrasonic clean washing the layer of mesh; and
glow discharging the layer of mesh.

3. The method of claim 1, wherein said preparing the layer of mesh comprises modifying the surface of the mesh by ion beam surface modification to provide a smooth surface and to ensure biocompatibility of the mesh and enhanced cell attachment to said mesh.

4. The method of claim 1, wherein said growing a biological matrix around the layer of mesh comprises modifying the surface of the mesh with an additive to ensure tissue growth.

5. The method of claim 4, wherein the additive is collagen, which applied to the layer of mesh to coat the layer of mesh to promote development of an interconnected pore network.

6. The method of claim 1, wherein said growing a biological matrix around the layer of mesh comprises seeding the at least three layers of cells sequentially on each side of the layer of mesh.

7. The method of claim 6, wherein a time interval of approximately two weeks is provided between seeding of each of the three different layers of cells.

8. The method of claim 1, wherein cytokines, including TGFβ1, are added with each sequentially seeded layer.

9. The method of claim 1, wherein the scaffold is configured to operate as an item selected from the group consisting of a heart valve and a vascular graft.

10. The method of claim 1, wherein the layer of mesh is a Nitinol mesh with a thickness between approximately 25 and 76 microns.

11. The method of claim 1, wherein the biological matrix is able to further grow and develop when implanted in vivo.

12. The method of claim 1, wherein the biological matrix is grown around the layer of mesh in vitro.

13. The method of claim 1, wherein the scaffold comprises a frame attached to the layer of mesh with the at least three layers of cells at each side of the mesh, wherein the frame is formed of a biocompatible metal and is covered with a woven polyester cloth.

14. The method of claim 1, wherein the mesh and at least three layers of cells at each side of the mesh are formed as leaflets, such that the scaffold is operable as a tissue heart valve.

15. The method of claim 14, wherein the scaffold includes at least two leaflets.

16. The method of claim 15, wherein the scaffold comprises a flexible frame having a saddle-shaped base with at least two upstanding posts, with the leaflets each having a peripheral free portion and a fixed portion, such that the peripheral free portion extends between the posts and the fixed portion is attached to the base.

17. The method of claim 16, wherein the scaffold comprises a frame having a base with three upstanding posts, with the leaflets attached to the frame and between the posts.

18. The method of claim 14, further comprising a flexible frame having a saddle-shaped base with at least two upstanding posts, with the leaflets each having a peripheral free portion and a fixed portion, such that the peripheral free portion extends between the posts and the fixed portion is attached to the base.

19. The method of claim 14, wherein the scaffold further comprises a frame having a base with three upstanding posts, with the leaflets attached to the frame and between the posts, and wherein the frame is formed of a biocompatible metal and is covered with a woven polyester cloth.

20. The method of claim 1, wherein the layer of mesh is a tubular wire mesh, wherein the at least three layers of cells at each side of the mesh are formed around the mesh to completely or partially conceal the mesh therein, whereby the scaffold is formed in the shape of a vessel to operate as a vascular graft.

21. The method of claim 1, wherein the mesh is cut to the shape of a heart valve leaflet.

22. The method of claim 21, wherein a plurality of leaflets are attached together to form a heart valve shape.

23. The method of claim 1, wherein the smooth muscle cell layer comprises vascular smooth muscle cells, the fibroblast/myofibroblast cell layer comprises vascular fibroblast/myofibroblast cells, and the third layer comprises vascular endothelial cells.

* * * * *